United States Patent
Rayek et al.

(10) Patent No.: US 10,575,981 B2
(45) Date of Patent: Mar. 3, 2020

(54) MULTI-APPLIANCE SYSTEM AND METHOD FOR TREATING OBSTRUCTIVE SLEEP APNEA AND CORRECTING MALOCCLUSION SIMULTANEOUSLY

(71) Applicants: Riaz Rayek, Aldie, VA (US); Jeffrey Tomcsik, Avenue, MD (US)

(72) Inventors: Riaz Rayek, Aldie, VA (US); Jeffrey Tomcsik, Avenue, MD (US)

(*) Notice: Subject to any disclaimer, the term of this patent is extended or adjusted under 35 U.S.C. 154(b) by 266 days.

(21) Appl. No.: 15/828,185

(22) Filed: Nov. 30, 2017

(65) Prior Publication Data

US 2018/0177628 A1 Jun. 28, 2018

Related U.S. Application Data

(63) Continuation of application No. 14/979,110, filed on Dec. 22, 2015, now Pat. No. 9,861,513.

(60) Provisional application No. 62/095,358, filed on Dec. 22, 2014.

(51) Int. Cl.
| | |
|---|---|
| *A61F 5/56* | (2006.01) |
| *A61C 7/08* | (2006.01) |
| *A61C 7/36* | (2006.01) |

(52) U.S. Cl.
CPC ............... *A61F 5/566* (2013.01); *A61C 7/08* (2013.01); *A61C 7/36* (2013.01)

(58) Field of Classification Search
CPC .............. A61F 5/566; A61C 7/08; A61C 7/36
USPC ....................................... 433/6; 128/859–861
See application file for complete search history.

(56) References Cited

U.S. PATENT DOCUMENTS

| | | | | |
|---|---|---|---|---|
| 5,683,244 | A * | 11/1997 | Truax .................. | A61C 7/00 433/24 |
| 6,604,527 | B1 * | 8/2003 | Palmisano .............. | A61C 7/08 128/848 |
| 8,136,529 | B2 * | 3/2012 | Kelly .................... | A61F 5/566 128/848 |
| 8,215,312 | B2 * | 7/2012 | Garabadian ............ | A61F 5/566 128/846 |
| 8,881,733 | B1 * | 11/2014 | Harkins ................ | A61F 5/566 128/848 |
| 9,744,006 | B2 * | 8/2017 | Ross .................... | A61C 7/36 |
| 9,861,513 | B2 * | 1/2018 | Rayek ................... | A61F 5/566 |
| 2014/0060549 | A1 * | 3/2014 | Lucas ................... | A61F 5/566 128/861 |
| 2014/0238415 | A1 * | 8/2014 | Lucas ................... | A61C 7/08 128/861 |
| 2018/0147028 | A1 * | 5/2018 | Warshawsky .......... | A61C 7/36 |

* cited by examiner

*Primary Examiner* — Yogesh P Patel
(74) *Attorney, Agent, or Firm* — McKinney & Associates, LLC; J. Andrews McKinney, Jr.

(57) ABSTRACT

A system and method for simultaneously (i) treating a patient's malocclusion by repositioning teeth from an initial tooth arrangement to a final tooth arrangement and (ii) treating Obstructive Sleep Apnea ("OSA") by forcing the mandible forward comprises a plurality of (e.g., 10-30) sets of individual appliances. The appliances are configured to be placed successively on the patient's upper and lower dental arches and to incrementally reposition the teeth and forcing the jaw forward, during sleep. The system of appliances is preferably configured at the outset of treatment so that the patient may progress through treatment without the need to have the treating professional perform each successive step in the procedure.

15 Claims, 3 Drawing Sheets

MULTI-APPLIANCE SYSTEM AND METHOD FOR TREATING OBSTRUCTIVE SLEEP APNEA AND CORRECTING MALOCCLUSION SIMULTANEOUSLY

PRIORITY CLAIM AND REFERENCE TO RELATED APPLICATION

This application is a Continuation of and claims priority to related and commonly owned co-pending U.S. nonprovisional patent application Ser. No. 14/979,110, filed Dec. 22, 2015 and also claims priority to provisional patent application No. 62/095,358, filed Dec. 22, 2014 and entitled System and Method for Treating Obstructive Sleep Apnea and Correcting Malocclusion Simultaneously, the entire disclosures of which are incorporated herein by reference.

BACKGROUND OF THE INVENTION

Field of the Invention

The present invention relates to appliances and methods for treating Obstructive Sleep Apnea and malocclusion correction.

Discussion of the Prior Art

Individuals with Obstructive Sleep Apnea ("OSA") may have small, retruded chins and crowded lower teeth that cause the tongue to be pushed back against the airway, causing constriction of the airway, one of the primary causes of OSA. The obstruction in OSA is, more specifically, partial or complete obstruction of the upper airway during sleep. Sleep apnea causes drops in the blood oxygenation level and often adversely affects the heart by increasing blood pressure and pulse rate. Many aspects of a person's quality of life (e.g., physical and emotional health) are affected by OSA.

A typical approach for treating OSA is two-pronged, first, the patient is treated with traditional orthodontic appliances (e.g., braces) to expand the lower teeth at least partially and, second, the patient is fitted with a Mandibular Advancement Splint (MAS) appliance to move the lower jaw forward at night to lessen the patient's obstruction.

This two pronged approach is intended to lessen the severity of and treat the symptoms of OSA. An example of a Mandibular Advancement Splint ("MAS") device is found in U.S. Pat. No. 6,604,527, which is incorporated by reference for the sole purpose of providing technical and anatomical nomenclature.

In the OSA patient, sagittal mandibular or lower jaw movement occurs within a range limited by the border movements, broadly characterized by the most protruded path of opening and closure, the maximal open position of the mandible, the occlusal positions and the most retarded path of closure. In this sense, a reference herein to mandibular advancement represents locating the mandible so that it functions in the protruded range from the reflex or habital path of closure (occurring between the intercuspal occlusal position and the maximum open position) to the protrusive border path. Treatments using the MAS dental appliance (e.g., 90, as shown in FIG. 1B) push the lower jaw forward, and this treatment essentially involves wearing an appliance with upper and lower segments that engage each other (e.g., upper and lower flanges 92, 94) when the mouth is closed and the lower jaw is pushed forward, opening the airway.

Another treatment for obstructive sleep apnea involves wearing and sleeping with a Continuous Positive Airway Pressure (CPAP) mask, which pushes pressurized air into the lungs to get past the obstruction. CPAP is a well-known therapy for treating sleep apnea. OSA patients wear a CPAP face or nasal mask during sleep. The mask, connected to a pump, provides a positive flow of air into the nasal passages in order to keep the airway open. The CPAP form of treatment is cumbersome, difficult, uncomfortable and disruptive for the bed partners.

Malocclusion is the misalignment of teeth and/or an incorrect relation between the teeth of the upper and lower dental arches, giving rise to faulty contact between upper and lower teeth. Sometimes skeletal disharmony of the face, and in particular an incorrect relationship between the maxilla and mandible, is a contributing factor or even the root cause of malocclusion. The MAS device and method for mandibular advancement described in U.S. Pat. No. 6,604,527 is not configured to correct malocclusion, which is why prior art methods may require simultaneous use of braces.

For patients who have no issues with OSA, orthodontic treatment for malocclusion can be addressed using traditional braces or "clear aligner" treatments such as those sold under the brand name Invisalign® by Alignment Technologies, Inc. Invisalign® appliances are typically provided in pairs (for upper and lower arches, e.g., 80, as shown in FIG. 1A) each configured as a thin concave trough of material that forms a receiving cavity geometry generally conforming to a patient's teeth but slightly out of alignment with the initial tooth configuration.

Clear aligner appliances are made using polymers such as thermoplastic polyurethane. Polymers may deform over time and use due to external and internal forces. Some deforming external forces may be encountered during include repeated insertions and removals and from actual use (e.g. while biting or wearing the aligners). An internal deforming force may include material stress relaxation. The deformation may reduce tooth moving forces, thereby reducing the usefulness of the dental appliance. Once the usefulness of the aligner dental appliance is reduced, the dental appliance is typically disposed of, and either a replacement dental appliance is made or the next dental appliance in the treatment series is used.

Clear aligners are like retainers (or trays) that move teeth over a period of time to correct misalignments, such as crowding. A series of aligners are made to treat each specific case, ranging from 10-30 aligners for an average patient. Patients typically wear a new set of aligners (upper and lower) every two weeks for a period of time as needed to make the alignment correction for the teeth.

The treatment for malocclusion and the treatment for OSA are completely separate and distinct modalities. Patients are treated orthodontically to expand the lower arch by correcting crowding (permanently) and a completely separate MSA appliance (e.g., 90, as shown in FIG. 1B) is also fitted to move their jaw (temporarily, while they sleep) to help with their breathing.

These two treatments (wearing braces and wearing an MSA splint) are problematic for the patient, since wearing braces (or clear aligners) makes wearing an MSA splint appliance awkward for some and impossible for others. There is a need, therefore, for a convenient, flexible, effective and unobtrusive system and method for treating OSA and correcting malocclusion which overcomes these problems.

OBJECTS AND SUMMARY OF THE INVENTION

Accordingly, it is an object of the present invention to overcome the above mentioned difficulties by providing an improved system and method for treating obstructive sleep apnea ("OSA") and correcting malocclusion simultaneously, without requiring the patient to simultaneously wear orthodontic braces or clear aligners with an incompatible, awkward Mandibular Advancement Splint ("MAS") appliance.

In accordance with the present invention, a method for treating obstructive sleep apnea and correcting malocclusion simultaneously includes using a series of combined use Mandibular Splint ("MS") aligner appliances in matching pairs having a first, upper MS-aligner and second lower MS-aligner; where the first MS-aligner is shaped to engage a patient's upper arch and the second aligner is shaped to engage the patent's lower arch, and where series of first and second MS-aligners, when used in sequence, are configured to correct a specific malocclusion for the patient. The upper MS-aligners all carry or incorporate at least one MS ridge member on each side, and the lower aligners all carry a MS fin member on each side. When the upper and lower MS aligners are fitted into the patient's mouth, each upper MS aligner ridge engages a corresponding low MS aligner's fin and prevents that cooperating fin from moving backwards, thereby preventing the lower arch (and mandible) of the patient from moving backwards, thus treating the patient's OSA symptoms.

Another object of the system and method of the present invention for treating obstructive sleep apnea and correcting malocclusion simultaneously is to provide a cost-beneficial solution for manufacturers and patients by providing an attachment to the upper and lower MS aligners to allow for the use of the same MS ridge and MS fin to be attached to each upper & lower set of aligners used by the patient during their treatment.

Another object of the system and method of the present invention for treating obstructive sleep apnea and correcting malocclusion simultaneously is to reduce the time needed for treatment. In accordance with the method of the present invention, treatment for both obstructive sleep apnea and correction of the malocclusion is simultaneously accomplished by the patient's insertion of the upper and lower MS aligners, thereby reducing the total time necessary, because treatment for the OSA does not have to be given before or after orthodontic treatment of a malocclusion.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

DESCRIPTION OF THE PREFERRED EMBODIMENT

Referring now to FIGS. 2-7, the present invention comprises a Multi-Appliance system and method for treating obstructive sleep apnea ("OSA") and correcting malocclusion simultaneously.

Figure 1A:
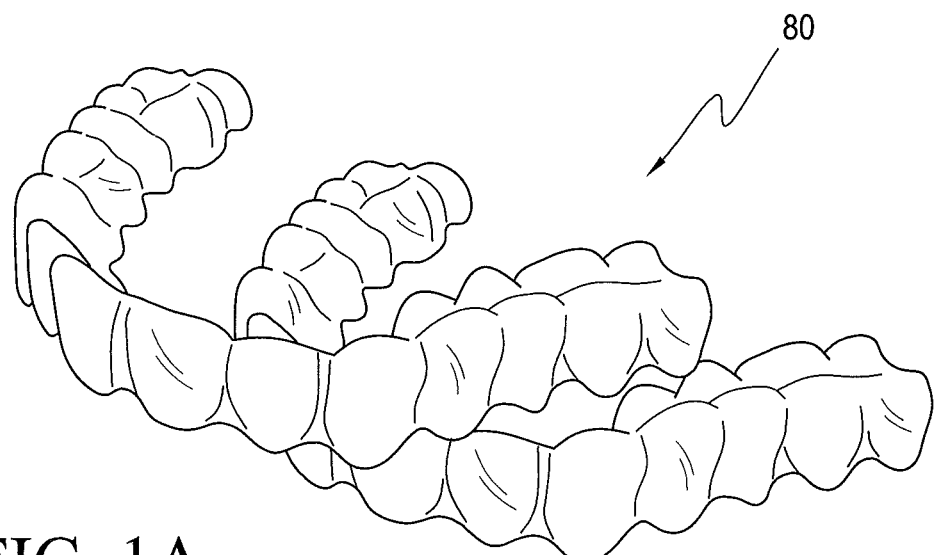
FIG. 1A illustrates a typical prior art Clear Aligner set, for purposes of establishing reference nomenclature.
Figure 1B:
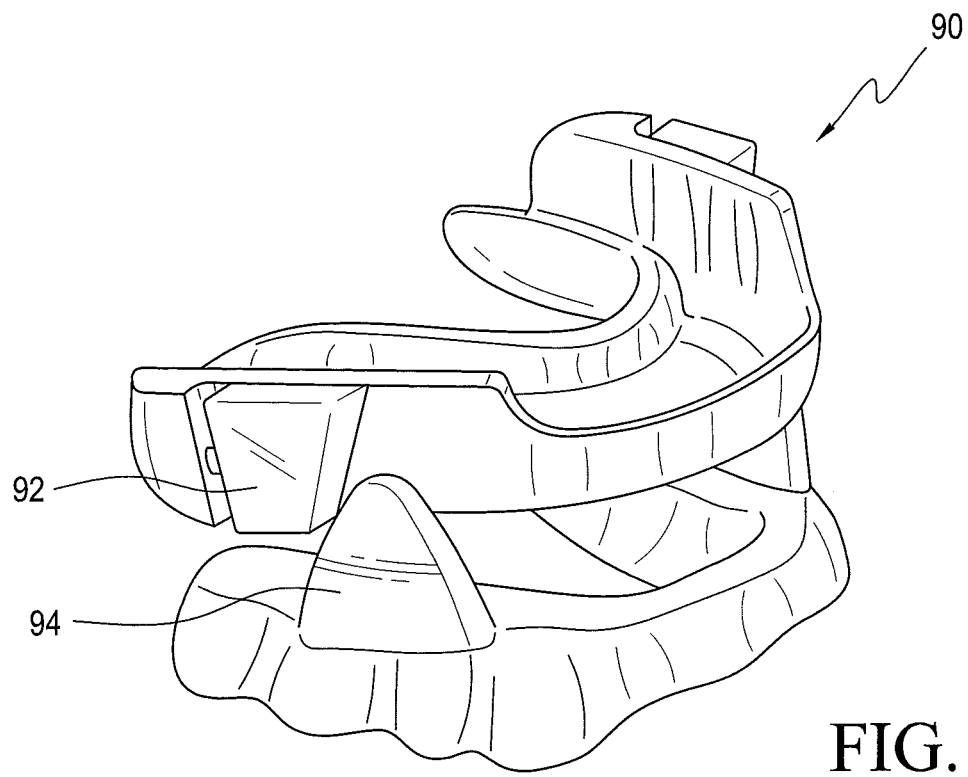
FIG. 1B illustrates a typical prior art mandibular advancement splint ("MAS") appliance, for purposes of establishing reference nomenclature.
Figure 2:
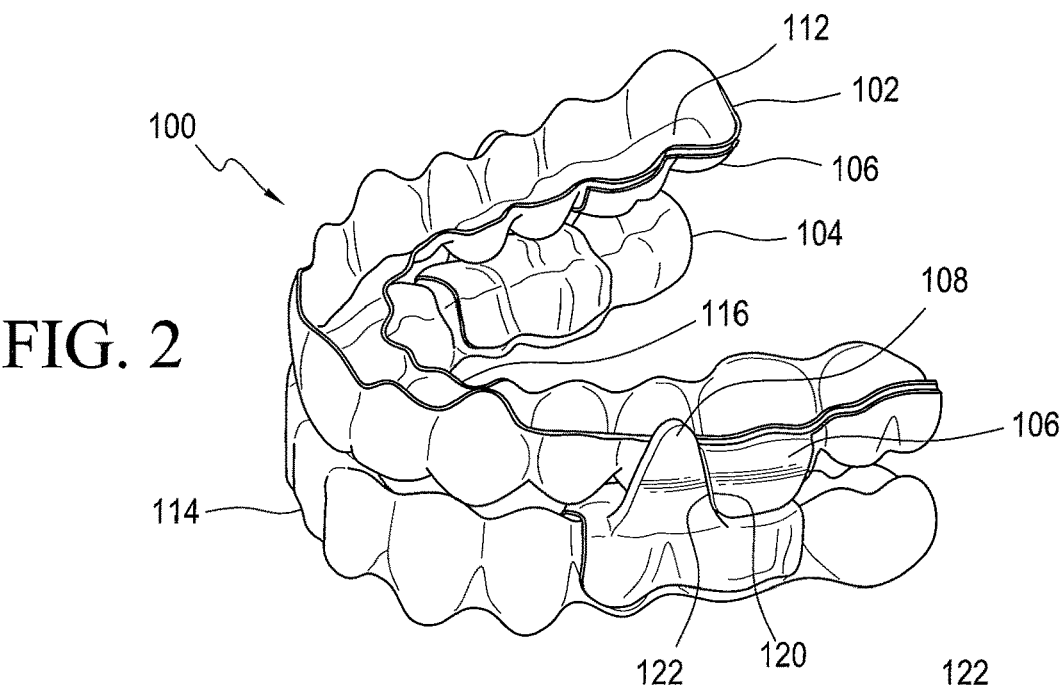
FIG. 2 illustrates a perspective view of Mandibular Splint ("MS") aligner appliance pair illustrating part of the system and method for treating obstructive sleep apnea ("OSA") and correcting malocclusion simultaneously, in accordance with the present invention.
Figure 3:
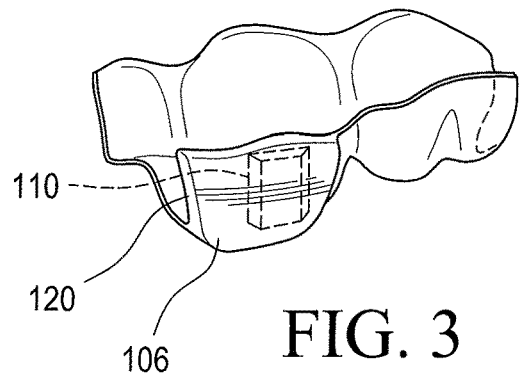
FIG. 3 illustrates, in perspective, a detailed segment view of an optional MS ridge member component adapted for removable attachment to and use with Mandibular Splint ("MS") aligner appliance of FIG. 2, showing a detailed view of the left side ridge's fin engagement surface, in accordance with the present invention.
Figure 5:
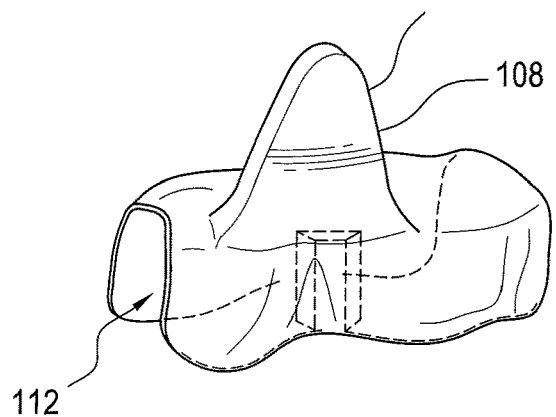
FIG. 5 illustrates, in perspective, a detailed segment view of an optional MS fin member component adapted for removable attachment to and use with Mandibular Splint ("MS") aligner appliance of FIG. 2, showing a detailed view of the left side fin's ridge engagement surface, in accordance with the present invention.
Figure 4:
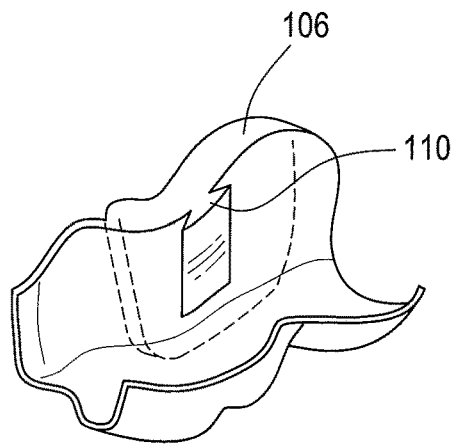
FIG. 4 illustrates, in perspective, a detailed segment view of an optional MS ridge member component adapted for removable attachment to and use with Mandibular Splint ("MS") aligner appliance of FIG. 2, showing a detailed view of the right side ridge's dove-tail shaped aligner-engagement tab, in accordance with the present invention.
Figure 6:
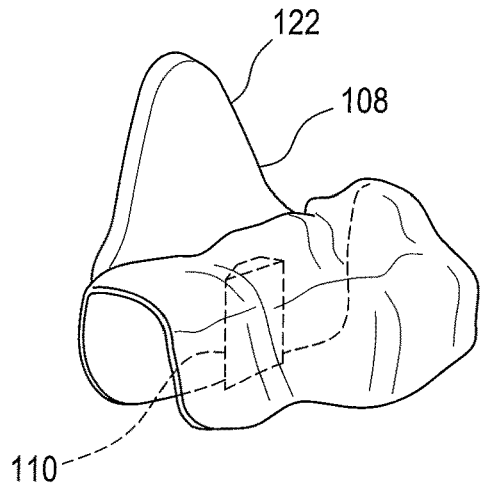
FIG. 6 illustrates, in perspective, a detailed segment view of an optional MS fin member component adapted for removable attachment to and use with Mandibular Splint ("MS") aligner appliance of FIG. 2, showing a detailed view of the right side fin's dove-tail shaped aligner-engagement tab, in accordance with the present invention.

Referring first to FIG. 2, Mandibular Splint ("MS") Aligner appliance 100 comprises first, upper MS-Aligner 102 and second lower MS-Aligner 104 which are configured as a set for use by a patient who will be fitted for and wear a sequence between 10 and 30 sets of Mandibular Splint ("MS") aligner appliances. The complete array of 10 and 30 sets of Mandibular Splint ("MS") aligner appliances, when used in sequence, are adapted to (a) reposition a specific patient's teeth (not shown) from an initial tooth arrangement to a final tooth arrangement over a period of time and correct malocclusion while simultaneously (b) treating the patient's OSA by pushing the lower jaw forward by having the MS aligner's Fin members 108 and Ridge members 106 engage each other when the patient's mouth is substantially closed and force the patient's lower jaw forward, thereby maintaining an un-occluded or open airway.

In accordance with the method of the present invention, obstructive sleep apnea and malocclusion are treated simultaneously using a series of (e.g. 10-30 sets of) combined use Mandibular Splint ("MS") aligner appliances 100 in matching pairs having a first, upper MS-aligner 102 and second, lower MS-aligner 104. The first, upper MS-aligner 102 is shaped to engage a patient's upper arch and the second, lower aligner 104 is shaped to engage the patent's lower arch. The series of first and second MS-aligners, when used in sequence, are configured to correct a specific malocclusion for the patient. The upper MS-aligners 102 (e.g., as illustrated in FIG. 2) all carry or incorporate at least one MS Ridge member 106 defining a fin engagement surface 120 on a selected side (e.g., left or right, and preferably one on each side, as shown in FIG. 2). The lower aligners 104 all carry at least one MS Fin member 108 on a selected side (e.g., left or right, and preferably one on each side, as shown in FIG. 2). When the upper and lower MS aligners 102, 104 are fitted into the patient's mouth, each upper MS aligner ridge engagement surface 120 engages and bears against a corresponding lower MS aligner's fin 108 and prevents that cooperating fin from moving backwards or proximally, thereby preventing the lower arch (and mandible) of the patient from moving backwards or proximally, thus treating the patient's OSA symptoms.

FIGS. 2-7 illustrate illustrative embodiments 100, 200 of the system and method for treating obstructive sleep apnea and correcting malocclusion simultaneously. More specifically, the system of the present invention comprises a series of dental appliances for simultaneously (i) treating a patient's malocclusion by repositioning teeth from an initial tooth arrangement to a final tooth arrangement and (ii) treating OSA by forcing the mandible forward. As noted above, a plurality of (e.g., 10-30) sets of individual appliances are configured to be placed successively on the patient's upper and lower dental arches to incrementally reposition the teeth from an initial tooth arrangement, through a plurality of intermediate tooth arrangements, and to a final tooth arrangement. The system of appliances (e.g., 100, 200) is usually configured at the outset of treatment so that the patient may progress through treatment without the need to have the treating professional perform each successive step in the procedure.

As shown in FIG. 2, an exemplary Mandibular Splint ("MS") aligner appliance 100 consists of set including an upper arch aligner 102 and lower arch aligner 104. Each arch aligner (102, 104) comprises a concave trough conforming closely to a specific patient's plurality of teeth and snugly engage the patent's teeth when placed over the teeth. The concave trough preferably comprises a shape memory material being transitionable to the approximate original shape from the relaxed shape upon application of an external stimulus. The original shape is configured to apply a desired force on a tooth when the trough conforms (upon placement on the patient's teeth). Each AS aligner has an inner cavity 112, a proximal edge 114, and a distal edge 116. The inner cavity is shaped to receive and resiliently reposition teeth from one tooth arrangement to a successive tooth arrangement, as is customarily done with successive use of standard clear aligner appliances. As noted above, clear aligner treatments are sold under the brand name Invisalign® by Alignment Technologies, Inc. The Invisalign® clear alignment systems and methods are described and illustrated in several patents including U.S. Pat. Nos. 6,471,511, 6,217, 325, 5,975,893, 6,705,863, 6,722,880, 7,125,248, 7,134,874, and 7,578,674, which are incorporated herein by reference for the sole purpose of providing technical and anatomical nomenclature.

The upper arch aligner 102 preferably comprises left side and right side (or first and second opposing) ridge members 106 and is firmly received and fitted over the upper teeth. The ridge features 106 are positioned upon and carried by an external surface of the aligner upper shell member 106 close to the segment configured for receiving the posterior teeth or larger molars.

The lower arch aligner shall member 104 preferably comprises left side and right side (or first and second opposing) upwardly projecting fin members 108 and is firmly received and fitted over the lower teeth. The fins 108 are positioned to cooperate with ridge features 106 and so are preferably positioned on an external surface of aligner lower shell member 104 beside and close to portion configured to receive the posterior teeth or larger molars.

The forward or leading edge 120 of each ridge 106 forms an angled engagement surface. The rearward or trailing edge 122 of each fin 108 defines a cooperating engagement surface which compliments, abuts and bears against the corresponding engagement surface of the leading edges 120 of the corresponding ridge 106, when the patient's mouth is closed.

As noted above, when correcting malocclusion it takes more than one set or pair of arch aligners (e.g., 104, 106) to make the correction. Over time, new pairs of aligners, an upper arch aligner and lower arch aligner, are needed to make a new incremental adjustment to the teeth to correct the malocclusion. In the system of the present invention, each set of aligners may be configured with permanent, molded in situ fins and ridges, or the fins and ridges (e.g., 106, 108) may be removably installed upon each arch aligner in the series of sets.

Thus, one embodiment of the present system and method has the ridges 106 and fins 108 affixed to each pair of arch aligners (102, 104). In this embodiment, if a user requires twenty pairs of arch aligners, then there will be twenty arch aligners each with a ridge 106 and fin 108 already affixed to each aligner before being given to the patient. Therefore there will be twenty sets of aligners 104, 106, each configured with ridges and fins positioned to treat that patient's malocclusion and OSA during a given evening's sleep.

In an alternative embodiment, the patient uses one set of ridges 106 and fins 108 for all of the pairs of arch aligners (102, 104) used for the correction of malocclusion. In this alternative embodiment, if a patient requires twenty pairs of arch aligners, there will only be one pair (left side and right side) of ridge members 106 and a corresponding pair of fin members 108 configured for use used for all twenty pairs of arch aligners. The ridges 106 and fins 108 are affixed to a pair of arch aligners (102, 104) by use of a dove-tail shaped aligner-engagement tab 110 which engages a corresponding dove-tail shaped engagement slot 211 defined in a side surface of the corresponding aligner (e.g., 202, 204, as illustrated in FIG. 7).

In the method of the present invention, releasably detachable MS fin members 208, and MS ridge members 206 provide the same functional and therapeutic benefits as the ridges 106 and fins 108 used in Mandibular Splint ("MS") aligner appliance 100, but the ridge members and fin members may be applied to selected aligner members or shells 202, 204 as those aligner shells are used, in sequence, allowing the patient or professional to decide when to use the MS fin members 208 and MD ridge members 206 and saving money, since the MS fin members and MD ridge members need not be discarded when used aligner shells are discarded.

Figure 7:
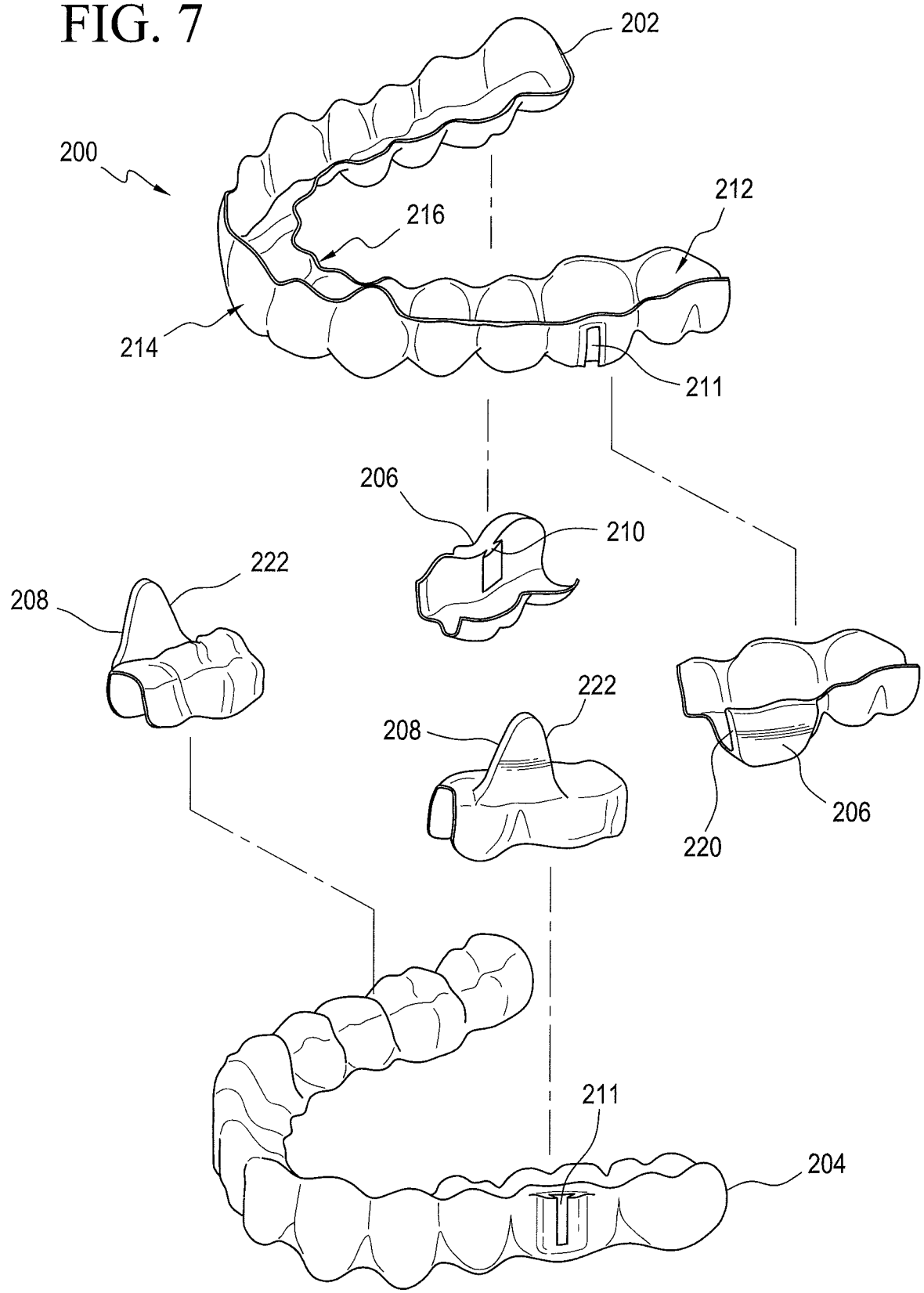
FIG. 7 illustrates, in perspective, an exploded view of a six-part Mandibular Splint ("MS") aligner appliance including an MS upper aligner and a MS lower aligner configured to releasably receive and carry the MS fin and ridge components of FIGS. 2-6, in accordance with the system and method of the present invention.

FIG. 7 illustrates the embodiment of the system 200 and method for treating obstructive sleep apnea and correcting malocclusion simultaneously, with selectively attachable and detachable MS fin members 208 and MD ridge members 206. Arch aligners (202, 204) have a releasable attachment feature or dove-tail slot or groove 211 which is configured to firmly receive a corresponding inwardly projecting attachment protuberance or feature 210 by sliding either ridge 206 or fin 208 into its respective groove 211 where it is preferably received and retained by friction fit so that there is no interference in the upper and lower alignment or "bite" of the aligners 202, 204, when worn by the patient. The leading edge 220 defined on the external surfaces of each ridge member 206 forms an angled or inclined engagement surface. The trailing edge 222 of each substantially triangular fin member 208 forms a cooperating angled engagement surface complementing the engagement surfaces of the leading edges 220 of ridges 206.

It will be appreciated by those of skill in the art that the system (e.g., 100, 200) for simultaneously treating obstructive sleep apnea and correcting malocclusion simultaneously comprises a number of features which, together, provide a surprisingly effective way for patients to overcome the problems with the prior art: namely (a) use of a first (102, 202) and second (104, 204) aligner, where the first aligner (102, 202) is shaped to engage the upper arch of a patient and the second aligner (104, 204) is shaped to engage the lower arch of the patient and the first and second aligners are configured to correct malocclusion of the patient;

(b) a ridge (106, 206), where the ridge is connected to the first aligner (102, 202); and (c) a fin (108, 208), where the fin is connected to the second aligner (104, 204); where the ridge (106, 206) engages with the fin (108, 208) and prevents the fin from moving backwards thereby preventing the lower arch of a patient from moving backwards.

The system for treating obstructive sleep apnea and correcting malocclusion simultaneously, comprises:

(a) a first (102, 202) and second (104, 204) aligner, where the first aligner (102, 202) is shaped to engage the upper arch of a user and the second aligner (104, 204) is shaped to engage the lower arch of the user and the first (102, 202) and second aligners (104, 204) are configured to correct malocclusion of the user;

(b) a ridge (106, 206), where the ridge is connected to the first aligner; and (c) a fin (108, 208), where the fin is connected to the second aligner;

where the ridge (106, 206) engages with the fin (108, 208) and prevents the fin (108, 208) from moving backwards thereby preventing the lower arch of a user from moving backwards and where the ridge (106, 206) is connected to the first aligner (102, 202) by an attachment (110, 210) and the fin (108, 208) is connected to the second aligner (104, 204) by an attachment (110, 210).

A system for treating obstructive sleep apnea and correcting malocclusion simultaneously, comprises:

(a) a first (102, 202) and second (104, 204) aligner, where the first aligner (102, 202) is shaped to engage the upper arch of a user and the second aligner (104, 204) is shaped to engage the lower arch of the user and the first (102, 202) and second (104, 204) aligners are configured to correct malocclusion and obstructive sleep apnea of the user;

(b) a ridge (106, 206), where the ridge is adapted onto the first aligner directly;

(c) a fin (108, 208), where the fin is adapted onto the second aligner directly; and where the ridge (106, 206) engages with the fin (108, 208) and prevents the fin (108, 208) from moving backwards thereby preventing the lower arch of a user from moving backwards.

An orthodontic device for treating obstructive sleep apnea and correcting malocclusion simultaneously comprises:

(a) a first (102, 202) and second (104, 204) aligner, where the first aligner (102, 202) is shaped to engage the upper arch of a user and the second aligner (104, 204) is shaped to engage the lower arch of the user and the first (102, 202) and second (104, 204) aligners are configured to correct malocclusion of the user;

(b) a ridge (106, 206), where the ridge is connected to the first aligner; and (c) a fin (108, 208), where the fin is connected to the second aligner;

where the ridge engages with the fin and prevents the fin from moving backwards thereby preventing the lower arch of a user from moving backwards.

A system for treating obstructive sleep apnea and correcting malocclusion simultaneously comprises:

(a) a first appliance (202, 204) having a geometry selected to reposition the teeth from the initial tooth arrangement to a first intermediate arrangement;

(b) one or more intermediate appliances (202, 204) having different teeth-receiving cavity geometries based on successive intermediate tooth arrangements, the geometries selected to progressively reposition the teeth from the first intermediate arrangement to successive intermediate arrangements; and (c) a final appliance (202, 204) having a geometry selected to progressively reposition the teeth from a last intermediate arrangement to the final tooth arrangement, where the appliances comprise polymeric shells having cavities 212 and where the teeth-receiving cavities of successive shells have different geometries shaped to receive and resiliently reposition teeth from one arrangement to a successive arrangement, where at least one of the successive intermediate tooth arrangements is generated prior to generating a preceding successive intermediate tooth arrangement, (d) where the first, intermediate, and final appliances have at least one lower component having an attachment structure 211 that is releasably attachable to at least a portion of the lower jaw and an engagement surface extending upwardly from the attachment structure 208; and at least one upper component having an attachment structure 211 that is releasably attachable to at least a portion of the upper jaw and an engagement surface extending downwardly from the attachment structure 206; and where, when the lower and upper engagement members are fitted to the jaws of a patient for use in sleep, the lower and upper engagement surfaces (206, 208) engage at a location lying in an area beside and close to the posterior teeth in a manner to cause advancement of the lower jaw from the reflex path of opening and maintain the engagement and advancement, while permitting sagittal movement, up to the normal range of jaw opening extending from an advanced occluding position by remaining fitted to the jaws of the patient when in use.

The method for treating obstructive sleep apnea and correcting malocclusion simultaneously using the systems (100, 200) described above comprises:

(a) providing a set of at least two dental incremental position adjustment appliances (202, 204) having different successive teeth-receiving cavity geometries 212 to a treating professional;

(b) subsequent to the providing step, placing a first incremental position adjustment appliance from the set of appliances in a patient's mouth, where the first appliance has a geometry selected to reposition the teeth from the initial tooth arrangement to the first intermediate arrangement;

where the dental incremental position adjustment appliances, having upper 206 and lower 208 components, to the jaws of a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by the components remaining fitted to the jaws of the patient simultaneously;

(c) successively replacing one or more additional appliances (202, 204) from the set in the patient's mouth with the next incremental position adjustment appliance of the set, where the additional appliances have geometries selected to progressively reposition the teeth from the first intermediate arrangement to successive intermediate arrangements and having upper 206 and lower 208 components, to the jaws of a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by the components remaining fitted to the jaws of the patient simultaneously; and (d) placing a final appliance into the patient's mouth, where the final appliance has a geometry selected to progressively reposition the teeth from a last intermediate arrangement to the final tooth arrangement, where the appliances comprise polymeric shells having cavities, and where the teeth-receiving cavities of successive shells have different geometries shaped to receive and resiliently reposition teeth form one arrangement to a successive arrangement and having upper 206 and lower 208 components, to the jaws of a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by the components remaining fitted to the jaws of the patient simultaneously.

Those of skill in the art will appreciate that the method and system of the present invention (e.g., 100, 200) make it possible to simultaneously treat obstructive sleep apnea and correct malocclusion simultaneously by combining a number of features to provide a surprisingly effective way for patients to overcome the problems with the prior art: namely, the multi-appliance system (e.g., 100, 200) which simultaneously (i) treats a patient's malocclusion by repositioning teeth from an initial tooth arrangement to a final tooth arrangement and (ii) treats OSA by forcing the mandible forward, wherein said system comprises a plurality of dental incremental position adjustment appliances including: (a) a first aligner appliance set comprising an upper arch appliance and a lower arch appliance, each having a geometry selected to reposition the teeth from the initial tooth arrangement to a first intermediate arrangement; (b) one or more intermediate aligner appliance sets having geometries selected to progressively reposition the teeth from the first intermediate arrangement to successive intermediate arrangements including a last intermediate arrangement; (c) a final aligner appliance set having a geometry selected to progressively reposition the teeth from the last intermediate arrangement to the final tooth arrangement, wherein the aligner appliances in each aligner appliance set comprise polymeric shells having cavities, wherein the cavities of successive shells have different geometries shaped to receive and resiliently reposition teeth from one arrangement to a successive arrangement; and (d) wherein at least one aligner said lower arch appliances appliance shell are each configured with slots to releasably receive and carry a carries a first mandible splint (MS) fin member configured to engage a surface on the appliance set's corresponding upper aligner appliance shell.

As described above and illustrated in FIGS. 2-7, at least one of the aligner appliance shell sets (and preferably all of the aligner appliance shell sets in a series) has a first MS upper arch member with a laterally projecting ridge member (e.g., 106, or 206) configured to cooperatively engage with and provide a forward jutting mandible biasing force against the first MS fin member (e.g., 122 or 222) when the aligner appliance set is worn on the patient's teeth.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the present invention as set forth in the appended claims.

We claim:

1. A system for treating obstructive sleep apnea ("OSA") and correcting malocclusion simultaneously, comprising:

(a) a combined use mandibular splint aligner appliance including a first aligner and a second aligner, wherein said first aligner is a first mandibular splint upper arch aligner appliance made from a shape memory polymer material and shaped to correct a specific malocclusion for a patient or user and engage the upper arch of said patient or user and said second aligner is a second mandibular splint lower arch aligner appliance made from a shape memory polymer material and shaped to correct said specific malocclusion for said patient or user and engage the lower arch of said patient or user wherein said first and second aligners are configured to engage the upper and lower arches and correct malocclusion of said user;

(b) a first mandibular splint ridge, wherein said mandibular splint ridge is connected to said first aligner; and (c) a first mandibular splint fin, wherein said mandibular splint fin is connected to said second aligner;

(d) wherein said mandibular splint ridge engages with said mandibular splint fin when the patient's jaws are closed, as during sleep, and prevents said mandibular splint fin from moving backwards thereby preventing said lower arch from moving backwards, wherein said mandibular splint ridge is carried on a ridge member made of polymer material and configured with an inwardly projecting dovetail-shaped aligner engagement tab to be releasably connected to a corresponding dovetail shaped slot or groove defined in said first aligner to provide releasable attachment thereto and said mandibular splint fin is carried on a fin member made of polymer material and configured with an inwardly projecting dovetail-shaped aligner engagement tab to be releasably connected to said second aligner and provide releasable attachment thereto.

2. The system of claim 1, wherein said second aligner further comprises:

(a) a second mandibular splint fin member made of shape memory polymer material and configured to be releasably connected to said second aligner by a releasable attachment feature, said second fin being configured to engage a second mandibular splint ridge on the first aligner;

(b) wherein said first mandibular splint fin is configured on a first (e.g., left) side of the aligner's sidewall surface the second mandibular splint fin is configured on a second (e.g., right) side of the aligner's sidewall, opposite the placement of the first mandibular splint fin member; and (c) wherein said first and second mandibular splint fin members include angled engagement surfaces configured to engage corresponding first and second engagement surfaces on the first (upper) aligner.

3. The system of claim 2, wherein said first and second aligners carry said first and second mandibular splint ridge members' angled engagement surfaces configured at a selected engagement angle, sloping proximally from top to bottom at said selected engagement angle of between 15 and 40 degrees from vertical, to cooperatively engage with and provide a mandible biasing force against said first and second mandibular splint fin members when said aligner appliance set is worn on the patient's teeth.

4. The system of claim 2, wherein said first aligner receives and supports said first and second MS ridge members' angled engagement surfaces configured at a selected engagement angle, sloping proximally from top to bottom at said selected engagement angle of approximately 30 degrees, to cooperatively engage with and provide a mandible biasing force against said first and second MS fin members when said aligner appliance set is worn on the patient's teeth.

5. An orthodontic system including a plurality of mandibular splint aligner appliances for simultaneously treating obstructive sleep apnea and correcting malocclusion, comprising:

(a) a first clear aligner made from a shape memory polymer material and shaped to engage a patient's upper arch and configured to correct the patient's upper arch malocclusion;

(b) a second clear aligner, made from a shape memory polymer material and shaped to engage a patient's lower arch and configured with said first clear aligner to correct the patient's lower arch malocclusion;

(c) said first aligner including and rigidly supporting at least one laterally projecting mandibular splint ridge member made from a shape memory polymer material and having a forward or distally facing ridge engagement surface; and (d) said first aligner including and rigidly supporting an upwardly projecting mandibular splint fin member made from a shape memory polymer material and having a rearward or proximally facing ridge engagement surface;

(e) wherein said mandibular splint ridge engages with said mandibular splint fin and prevents said fin from moving backwards or proximally when the first and second aligners are worn by the patient, whose mouth is closed, as when sleeping, thereby preventing the patient's lower arch and mandible from moving backwards or proximally; and (f) wherein said mandibular splint ridge member is connected to said first clear aligner by a first releasable attachment feature and said mandibular splint fin member is connected to said second clear aligner by a second releasable attachment feature, wherein said mandibular splint ridge member is connected to said first clear aligner by a first releasable attachment feature configured as an inwardly projecting dovetail-shaped aligner engagement tab and said mandibular splint fin member is connected to said second clear aligner by a second releasable attachment feature configured as an inwardly projecting dovetail-shaped aligner engagement tab.

6. The orthodontic system of claim 5, wherein said second aligner further comprises:

(a) a second mandibular splint fin made of shape memory polymer material and configured to engage a second mandibular splint ridge on the first aligner;

(b) wherein said first mandibular splint fin is configured on a first (e.g., left) side of the aligner's sidewall surface the second mandibular splint fin is configured on a second (e.g., right) side of the aligner's sidewall, opposite the placement of the first mandibular splint fin member; and (c) wherein said first and second mandibular splint fin members include angled engagement surfaces configured to engage corresponding first and second engagement surfaces on the first (upper) aligner.

7. The orthodontic system of claim 6, wherein said aligners carry said first and second mandibular splint ridge members' angled engagement surfaces configured at a selected engagement angle, sloping proximally from top to bottom at said selected engagement angle of between 15 and 40 degrees from vertical, to cooperatively engage with and provide a mandible biasing force against said first and second mandibular splint fin members when said first clear aligner and said second clear aligner are worn on the patient's teeth.

8. The orthodontic system of claim 6, wherein said aligners carry said first and second mandibular splint ridge members' angled engagement surfaces configured at a selected engagement angle, sloping proximally from top to bottom at said selected engagement angle of approximately 30 degrees, to cooperatively engage with and provide a mandible biasing force against said first and second mandibular splint fin members when said first clear aligner and said second clear aligner are worn on the patient's teeth.

9. A multi-appliance orthodontic treatment system for simultaneously treating a patient's obstructive sleep apnea and correcting malocclusion, comprising:

(a) a first aligner appliance shell made from a shape memory polymer material and having an internal cavity geometry selected to reposition the patient's teeth from an initial tooth arrangement to a first intermediate tooth arrangement;

(b) one or more intermediate appliance shells made from a shape memory polymer material and having different teeth-receiving cavity geometries based on successive intermediate tooth arrangements, the geometries selected to progressively reposition the patient's teeth from the first intermediate arrangement to successive intermediate arrangements; and (c) a final appliance shell made from a shape memory polymer material and having an internal cavity geometry selected to progressively reposition the teeth from a last intermediate arrangement to the final tooth arrangement, wherein the appliance shells have cavities configured specifically for the patient and wherein the teeth-receiving cavities of successive shells have different geometries shaped to receive and resiliently reposition teeth from one arrangement to a successive arrangement, wherein at least one of the successive intermediate tooth arrangements is generated prior to generating a preceding successive intermediate tooth arrangement, and (d) wherein said first, intermediate, and final appliances have at least one lower mandibular splint component having an attachment structure that is releasably attachable to at least a portion of the lower jaw and an engagement surface extending upwardly from said attachment structure; and at least one upper mandibular splint component having an attachment structure that is releasably attachable to at least a portion of the upper jaw and an engagement surface extending laterally from said attachment structure; and (e) wherein, when the lower and upper mandibular splint components are fitted to the jaws of a patient for use in sleep, and wherein the lower and upper engagement surfaces engage at a location lying in an area beside and close to the posterior teeth in a manner to cause advancement of the lower jaw from the reflex path of opening and maintain the engagement and advancement, while permitting sagittal movement, up to the normal range of jaw opening extending from an advanced occluding position by remaining fitted to the jaws of the patient when in use.

10. The multi-appliance orthodontic treatment system of claim 9, wherein said lower mandibular splint component in each set is a lower arch aligner which includes:

(a) a second attachment structure with a second lower component engagement surface configured to engage a second upper component engagement surface on said upper component;

(b) wherein said first lower component engagement surface is configured as a first mandibular splint fin projecting vertically from a sidewall configured on a first (e.g., left) side of the lower component's sidewall surface and a second lower component engagement surface is configured as a second mandibular splint fin projecting vertically from an opposing sidewall on a second (e.g., right) side of the lower component's sidewall surface, opposite the placement of the first fin member; and (c) wherein said first and second mandibular splint fin members include angled engagement surfaces configured to engage corresponding first and second engagement surfaces on the upper component.

11. The multi-appliance orthodontic treatment system of claim 10, wherein said upper mandibular splint components comprise upper aligners which carry said first and second mandibular splint ridge members having angled engagement surfaces configured at a selected engagement angle, sloping proximally from top to bottom at said selected engagement angle of between 15 and 40 degrees from vertical, to cooperatively engage with and provide a mandible biasing force against said first and second fin members when said upper and lower component set is worn on the patient's teeth.

12. The multi-appliance orthodontic treatment system of claim 10, wherein said upper components comprise upper aligners which carry said first and second mandibular splint ridge members having angled engagement surfaces configured at a selected engagement angle, sloping proximally from top to bottom at said selected engagement angle of approximately 30 degrees from vertical, to cooperatively engage with and provide a mandible biasing force against said first and second fin members when said upper and lower component set is worn on the patient's teeth.

13. A system for simultaneously (i) treating a patient's malocclusion by repositioning teeth from an initial tooth arrangement to a final tooth arrangement and (ii) treating OSA by forcing the mandible forward, said system comprising a plurality of dental incremental position adjustment appliances including:

(a) a first aligner appliance set comprising an upper arch appliance and a lower arch appliance, each having a geometry selected to reposition the teeth from the initial tooth arrangement to a first intermediate arrangement;

(b) one or more intermediate aligner appliance sets having geometries selected to progressively reposition the teeth from the first intermediate arrangement to successive intermediate arrangements including a last intermediate arrangement;

(c) a final aligner appliance set having a geometry selected to progressively reposition the teeth from the last intermediate arrangement to the final tooth arrangement, wherein the aligner appliances in each aligner appliance set comprise polymeric shells having cavities, wherein the cavities of successive shells have different geometries shaped to receive and resiliently reposition teeth from one arrangement to a successive arrangement; and (d) wherein at least one aligner said lower arch appliances appliance shell are each configured with slots to releasably receive and carry a carries a first mandible splint (MS) fin member configured to engage a surface on the appliance set's corresponding upper aligner appliance shell, wherein at least one of said aligner appliance shells carries a first MS upper arch appliances carry a laterally projecting ridge member configured to cooperatively engage with and provide a mandible biasing force against said first MS fin member when said aligner appliance set is worn on the patient's teeth, wherein each of said aligner appliance shell sets further comprises: (a) a second mandible splint (MS) fin member configured to engage a second surface on the upper aligner arch appliance shell, (b) wherein said first mandible splint (MS) fin member is configured on a first (e.g., left) side of the upper aligner arch appliance shell while the second mandible splint (MS) fin member is configured on a second (e.g., right) side of the upper aligner arch appliance shell, opposite the placement of the first mandible splint (MS) fin member; and (c) wherein said first and second mandible splint members are each configured to engage corresponding first and second surfaces on the upper aligner arch appliance shell.

14. The system of claim 13, wherein at least one of said aligner upper arch appliances shells carries a first and second MS ridge members configured to cooperatively engage with and provide a mandible biasing force against said first and second MS fin members when said upper arch aligner appliance set is worn on the patient's teeth.

15. The system of claim 14, wherein at least one of said upper arch aligner appliances shells further comprises releasable attachment receiving features (e.g., slots) adapted to releasably receive and retain said MS fin member ridge members.

* * * * *